United States Patent [19]

Chandraratna

[11] Patent Number: 5,516,904
[45] Date of Patent: May 14, 1996

[54] ACETYLENES DISUBSTITUTED WITH A HETEROAROMATIC GROUP AND A SUBSTITUTED PHENYL GROUP HAVING RETINOID LIKE ACTIVITY

[75] Inventor: Roshantha A. S. Chandraratna, El Toro, Calif.

[73] Assignee: Allergan, Inc., Irvine, Calif.

[21] Appl. No.: 384,886

[22] Filed: Feb. 7, 1995

Related U.S. Application Data

[62] Division of Ser. No. 126,952, Sep. 24, 1993, Pat. No. 5,414,007, which is a division of Ser. No. 967,889, Oct. 28, 1992, Pat. No. 5,264,456, which is a division of Ser. No. 669,696, Mar. 14, 1991, Pat. No. 5,175,185, which is a division of Ser. No. 458,963, Dec. 29, 1989, Pat. No. 5,013,744.

[51] Int. Cl.⁶ .................................................. A61K 31/425
[52] U.S. Cl. .......................... 514/269; 514/258; 544/298; 544/335
[58] Field of Search ................................... 514/258, 269; 544/298, 335

[56] References Cited

U.S. PATENT DOCUMENTS

| | | |
|---|---|---|
| 4,096,341 | 6/1978 | Frazer . |
| 4,326,055 | 4/1982 | Loeliger . |
| 4,391,731 | 7/1983 | Boller et al. ........................ 252/299.62 |
| 4,508,560 | 4/1985 | Brunner et al. ......................... 544/331 |
| 4,663,334 | 5/1987 | Carson .................................... 544/298 |
| 4,695,649 | 9/1987 | Magami et al. . |
| 4,723,028 | 2/1988 | Shudo . |
| 4,739,098 | 4/1988 | Chandraratna . |
| 4,740,519 | 4/1988 | Shroot et al. . |
| 4,798,893 | 1/1989 | Cherry et al. ........................... 544/299 |
| 4,810,804 | 3/1989 | Chandraratna . |
| 4,826,969 | 5/1989 | Maignan et al. . |
| 4,826,984 | 5/1989 | Berlin et al. ............................ 546/134 |
| 4,855,320 | 8/1989 | Chatterjee et al. . |
| 4,895,868 | 1/1990 | Chandraratna . |
| 4,927,947 | 5/1990 | Chandraratna ......................... 549/484 |
| 4,980,369 | 12/1990 | Chandraratna . |
| 4,992,468 | 2/1991 | Chandraratna . |

(List continued on next page.)

FOREIGN PATENT DOCUMENTS

| | | |
|---|---|---|
| 0098591 | 1/1984 | European Pat. Off. . |
| 0130795 | 1/1985 | European Pat. Off. . |
| 170105A | 2/1986 | European Pat. Off. . |
| 0176033 | 4/1986 | European Pat. Off. . |
| 0176032 | 4/1986 | European Pat. Off. . |
| 176034A | 4/1986 | European Pat. Off. . |
| 0253302 | 1/1988 | European Pat. Off. . |
| 0272921 | 6/1988 | European Pat. Off. . |
| 0284288 | 9/1988 | European Pat. Off. . |
| 0303915 | 2/1989 | European Pat. Off. . |
| 0315071 | 5/1989 | European Pat. Off. . |
| 0350846 | 7/1989 | European Pat. Off. . |
| 3316932 | 11/1983 | Germany . |
| 3524199 | 1/1986 | Germany . |
| 3602473 | 7/1987 | Germany . |
| 3708060 | 9/1987 | Germany . |
| 3715955 | 11/1987 | Germany . |
| 2190378 | 11/1987 | United Kingdom . |
| 8500806 | 2/1985 | WIPO . |
| 8504652 | 10/1985 | WIPO . |
| WO9116051 | 10/1991 | WIPO . |
| WO9206948 | 4/1992 | WIPO . |

OTHER PUBLICATIONS

A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43 No. 2, 1978 p. 358.

Conversion of Methyl Ketones into Terminal Acetylenes and (E)–Tri–substituted Olefins and Terpenoid Origin by Ei–i–chi, Anthony O. King, and William L. Klima, *J. Org. Chem.* 45 No. 12, 1980 p. 2526.

Sporn et al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 1980 pp. 627–630.

Shudo et al. in *Chem. Phar. Bull.* 33:404–407 (1985).

Kagechika et. al. in *J. Med. Chem.* 31:2182–2192 (1988).

Chemistry and Biology of Synthetic Retinoids by Marcia I. Dawson and William H. Okamura, published by CRC Press Inc., 1990, pp. 334–335, 354.

(List continued on next page.)

*Primary Examiner*—Donald G. Daus
*Attorney, Agent, or Firm*—Gabor L. Szekeres; Robert J. Baran; Martin A. Voet

[57] ABSTRACT

Retinoid like activity is exhibited by compounds of the formula

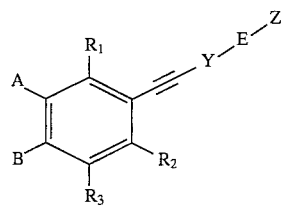

where $R_1$–$R_3$ independently are hydrogen, lower alkyl, cycloalkyl or lower alkenyl, A and B independently are hydrogen, lower alkyl, cycloalkyl, lower alkenyl, $SR_4$ or $OR_4$ where $R_4$ is lower alkyl, cycloalkyl or lower alkenyl; Y is selected from a group consisting of pyridazinyl, pyrimidinyl, pyrazinyl or oxazolyl; E is lower alkenyl, lower alkynyl, lower cycloalkyl, lower branched chain alkyl, or is characterized by the formula $(CH_2)_n$ where n is 0–5, and Z is H, OH, $OR_5$, $OCOR_5$, —COOH or a pharmaceutically acceptable salt, ester or amide thereof, —$CH_2OH$, $CH_2OR_6$, $CH_2OCOR_6$, or —CHO, $CH(OR_7)_2$, $CHOR_8O$, or $COR_9$, $CR_9(OR_7)_2$, $CR_9OR_8O$ where $R_5$ is lower alkyl, phenyl or lower alkylphenyl, $R_6$ is lower alkyl, phenyl or lower alkylphenyl, $R_7$ is lower alkyl, $R_8$ is a divalent alkyl radical of 2–5 carbons, and $R_9$ is an alkyl, cycloalkyl or alkenyl group containing 1 to 5 carbons.

13 Claims, No Drawings

OTHER PUBLICATIONS

Synthesis of 2,2'-Diacyl-1,1'-biaryls. Regiocontrolled Protection of . . . by Mervic, et al, *J. Org. Chem.*, No. 45, pp. 4720–4725, 1980.

A Dopamine Receptor Model and Its Application in the Design of a New Class of Rigid Pyrrolo[2,3-g]isoquinoline Antipsychotics, Gary L. Olson, et al., *American Chemical Society*, 1981, Vo. 24, No. 9, pp. 1026–1031.

6.2.3 Conformational Restriction, Williams, et al., *Drug Discovery and Development*, 1987 The Humana Press, pp. 54–55.

V. Retinoid Structure–Biological Activity Relationships, Chemistry and Biology of Synthetic Retinoids, pp. 324–356, 1990.

Davis et al. *J. Organomettalic Chem* 387 (1990) 381–390.

Effects of 13-Cis-Retinoic Acid, All-Trans-Retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792–797.

Organ maintenance of human sebaceous glands: in vitro effects of 13-cis retinoic acid and testosterone, John Ridden, et al., *Journal of Cell Science*, Vo. 95, 1990, pp. 125–136.

Characterization of Human Sebaceous Cells In Vitro, Thomas I. Doran, et al., *The Journal of Investigative Dermatology*, vol. 96, No. 3, Mar. 1991.

Synthesis and Evaluation of Stilbene and Dihydrostilbene Derivatives as Potential Anticancer Agents That Inhibit Tubulin Polymerization by Cushman, Mark et.al. *J.Med. Chem* 1991, 34, 2579–2588.

Synthesis and Evaluation of New Protein–Tyrosine Kinase Inhibitors. Part 1. Pyridine–Containing Stilbenes and Amides by Cushman, Mark et al., *Bioorganic & Medicinal Chemistry Letters*, vol. 1, No.4, pp. 211–214, 1991.

Di-and Tri-methoxystyryl Derivatives of Heterocyclic Nitrogen Compounds by Bahner, C. T. et al. Arzneim–Forsch./Drug Res, 31 (I), Nr. 3 (1981).

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry*, 1989, 32, pp. 1098–1108.

U.S. PATENT DOCUMENTS

| Patent No. | Date | Inventor | Class |
|---|---|---|---|
| 5,006,550 | 4/1991 | Chandraratna . | |
| 5,013,744 | 5/1991 | Chandraratna . | |
| 5,015,658 | 5/1991 | Chandraratna . | |
| 5,023,341 | 6/1991 | Chandraratna . | |
| 5,037,825 | 8/1991 | Klaus et al. | 514/233.8 |
| 5,045,551 | 9/1991 | Chandraratna . | |
| 5,053,523 | 10/1991 | Chandraratna . | |
| 5,068,053 | 11/1991 | Rieffenrath et al. | 544/298 |
| 5,068,252 | 11/1991 | Chandraratna . | |
| 5,089,509 | 2/1992 | Chandraratna . | |
| 5,130,335 | 7/1992 | Chandraratna . | |
| 5,134,159 | 7/1992 | Chandraratna . | |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 514/532 |
| 5,230,827 | 7/1993 | Rieffenrath et al. | 544/298 |
| 5,231,113 | 7/1993 | Chandraratna | 514/510 |
| 5,234,926 | 8/1993 | Chandraratna | 514/253 |
| 5,236,620 | 8/1993 | Rieffenrath et al. | 544/298 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |

ACETYLENES DISUBSTITUTED WITH A HETEROAROMATIC GROUP AND A SUBSTITUTED PHENYL GROUP HAVING RETINOID LIKE ACTIVITY

CROSS-REFERENCE TO RELATED APPLICATION

The present application is a divisional of application Ser. No. 08/126,952 filed on Sep. 24, 1993 now U.S. Pat. No. 5,414,007, which is a divisional of application Ser. No. 07/967,889, filed on Oct. 28, 1992, now issued as U.S. Pat. No. 5,264,456, which was a divisional of application Ser. No. 07/669,696, filed on Mar. 14, 1991, issued as U.S. Pat. No. 5,175,185, which in turn was a divisional of application Ser. No. 07/458,963 filed on Dec. 29, 1989, issued as U.S. Pat. No. 5,013,744.

BACKGROUND

This invention relates to novel compounds having retinoid like activity. More specifically, the invention relates to compounds having a substituted heteroaromatic portion and a substituted phenyl portion both of which are linked to an ethynyl moiety.

RELATED ART

Carboxylic acid derivatives useful for inhibiting the degeneration of cartilage of the general formula 4-(2-(4,4-dimethyl-6-X)-2-methylvinyl)benzoic acid where X is tetrahydroquinolinyl, chromanyl or thiochromanyl are disclosed in European Patent Application 0133795 published Jan. 9, 1985. See also European Patent Application 176034A published Apr. 2, 1986 where tetrahydronaphthalene compounds having an ethynylbenzoic acid group are disclosed, and U.S. Pat. No. 4,739,098 where three olefinic units from the acid-containing moiety of retinoic acid are replaced by an ethynylphenyl functionality.

SUMMARY OF THE INVENTION

This invention covers compounds of Formula 1

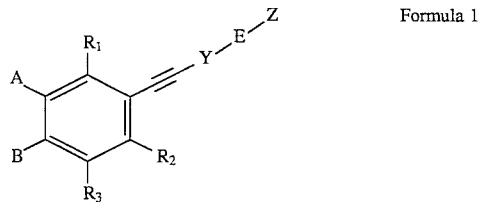

Formula 1 wherein $R_1$–$R_3$ independently are hydrogen, lower alkyl, cycloalkyl or lower alkenyl, A and B independently are hydrogen, lower alkyl, cycloalkyl, lower alkenyl, $SR_4$ or $OR_4$ where $R_4$ is lower alkyl, lower cycloalkyl or lower alkenyl; Y is selected from a group consisting of pyridazinyl, pyrimidinyl, pyrazinyl or oxazolyl; E is lower alkenyl, lower alkynyl, lower cycloalkyl, lower branched chain alkyl, or is characterized by the formula $(CH_2)_n$ where n is 0–5, and Z is H, OH, $OR_5$, $OCOR_5$, —COOH or a pharmaceutically acceptable salt, ester or amide thereof, —$CH_2OH$, $CH_2OR_6$, $CH_2OCOR_6$, or —CHO, $CH(OR_7)_2$, $CHOR_8O$, or $COR_9$, $CR_9(OR_7)_2$, $CR_9OR_8O$ where $R_5$ is lower alkyl, phenyl or lower alkylphenyl, $R_6$ is lower alkyl, phenyl or lower alkylphenyl, $R_7$ is lower alkyl, $R_8$ is a divalent alkyl radical of 2–5 carbons, and $R_9$ is an alkyl, cycloalkyl or alkenyl group containing 1 to 5 carbons.

In a second aspect, this invention relates to the use of the compounds of Formula 1 for treating dermatoses, such as acne, Darier's disease, psoriasis, icthyosis, eczema, atopic dermatitis and epithelial cancers. These compounds are also useful in the treatment of arthritic diseases and other immunological disorders (e.g. lupus erythematosus), in promoting wound healing, in treating dry eye syndrome and in delaying sun damage or reversing the effects of sun damage to skin. The compounds are further useful for treating disorders of gut epithelial differentiation, such as ileitis colitis and Krohn's disease.

This invention also relates to a pharmaceutical formulation comprising a compound of Formula 1 in admixture with a pharmaceutically acceptable excipient.

In another aspect, this invention relates to the process for making a compound of Formula 1 which process comprises reacting a compound of Formula 2 with a compound of Formula 3 in the presence of cuprous iodide and $Pd(PQ_3)_2Cl_2$ (Q is phenyl) or a similar complex

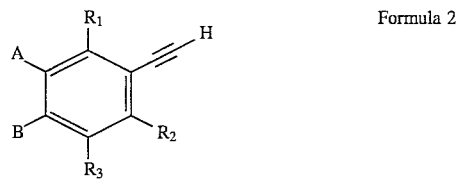

Formula 2

Formula 3 where $R_1$–$R_3$ are the same as described above, X is a halogen, preferably iodine; A, B, E, and Y are the same as defined above; and Z is H, or an ester or an amide, or a protected or unprotected acid, alcohol, aldehyde or ketone, giving the corresponding compound of Formula 1; or to the process of making a compound of Formula 1 which consists of reacting a zinc salt of a compound shown in Formula 2 with a compound of Formula 3 in the presence of $Pd(PQ_3)_4$ (Q is phenyl) or a similar complex.

In still another aspect, the present invention also relates to preparation of compounds of Formula 1 by conversion of compounds having the structure of Formula 4.

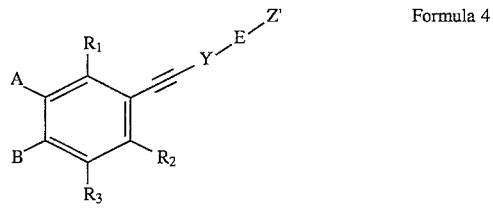

Formula 4

In Formula 4 the symbols A, B, $R_1$–$R_3$, Y and E are defined as above in connection with Formula 1, and Z' symbolizes such precursors of the group Z which can be readily converted by reactions well known to organic chemists, into the desired Z group. Thus, the present invention also relates to the above-noted processes involvings steps such as:

converting an acid of Formula 4 to a salt; or forming an acid addition salt;

converting an acid of Formula 4 to an ester; or converting an acid or ester of Formula 4 to an amide; or reducing an acid or ester of Formula 4 to an alcohol or aldehyde; or converting an alcohol of Formula 4 to an ether or ester; or oxidizing an alcohol of Formula 4 to an aldehyde; or converting an aldehyde of Formula 4 to an acetal; or converting a ketone of Formula 4 to a ketal, extending by homologation the length of the alkyl chain of a compound of Formula 4.

General Embodiments

Definitions

The term "ester" as used here refers to and covers any compound falling within the definition of that term as classically used in organic chemistry. Where Z (of Formula 1) is —COOH, this term covers the products derived from treatment of this function with alcohols. Where the ester is derived from compounds where Z is —CH$_2$OH, this term covers compounds of the formula —CH$_2$OOCR$_6$ where R$_6$ is any substituted or unsubstituted aliphatic, aromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Here, and where ever else used, lower alkyl means having 1–8 carbon atoms and includes straight, branched chained and cycloalkyl groups as well. Also preferred are the phenyl or lower alkylphenyl esters.

Amide has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR$_7$)$_2$. Here, R$_7$ is lower alkyl. Also, K may be —OR$_8$O— where R' is lower alkyl of 2–5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of this invention are those where the ethynyl group and the Z group are attached to the 2 and 5 positions respectively of a pyridine ring (the 6 and 3 positions in the nicotinic acid nomenclature being equivalent to the 2/5 designation in the pyridine nomenclature) or the 5 and 2 positions respectively of a thiophene group respectively; n is 0; and Z is —COOH, an alkali metal salt or organic amine salt, or a lower alkyl ester, or —CH$_2$OH and the lower alkyl esters and ethers thereof, or —CHO and acetal derivaives thereof. The more preferred compounds shown in Formula 5 are:

ethyl 6-(3-tert butylphenyl)-ethynyl nicotinate (Compound 1, A=(CH$_3$)$_3$C, B=H, R$_{10}$=CH$_2$—CH$_3$);

6-(3-tert butylphenyl)-ethynyl nicotinic acid (Compound 2, A=(CH$_3$)$_3$C, B=H, R$_{10}$=H;

ethyl 6-(4-tert butylphenyl)-ethynyl nicotinate (Compound 3, A=H, B=(CH$_3$)$_3$C, R$_{10}$=CH$_2$—CH$_3$);

6-(4-tert butylphenyl)-ethynyl nicotinic acid (Compound 4, A=H, B=(CH$_3$)$_3$C, R$_{10}$=H);

ethyl 6-[4-(4-methylpentyl)phenyl-ethynyl]nicotinate (Compound 5, A=H, B=(CH$_3$)$_2$CH—(CH$_2$)$_3$, R$_{10}$=CH$_2$—CH$_3$), and 6-[4-(4-methylpentyl)phenyl-ethynyl]nicotinic acid (Compound 6, A=H, B=(CH$_3$)$_2$CH—(CH$_2$)$_3$, R$_{10}$=H.

Ethyl 6-[4-(1,1,4-trimethylpentyl)phenylethynyl]nicotinate. (Compound 6a. A=H, B=(CH$_3$)$_2$CH(CH$_2$)$_2$C(CH$_3$)$_2$, R$_{10}$=CH$_2$CH$_3$ 6-[4-(1,1,4-trimethylpentyl)phenylethynyl nicotinic acid (Compound 6b, A=H, B=(CH$_3$)$_2$CH(CH$_2$)$_2$C(CH$_3$)$_2$, R$_{10}$=H ethyl 6-(3-thio-tert-butoxyphenyl)-ethynyl nicotinate (Compound 7, A=(CH$_3$)$_3$CS, B=H, R$_{10}$=CH$_2$—CH$_3$);

6-(3-thio-tert-butoxyphenyl)-ethynyl nicotinic acid (Compound 8, A=(CH$_3$)$_3$CS, B=H, R$_{10}$=H);

ethyl 6-(4-thio-tert-butoxyphenyl)-ethynyl nicotinate (Compound 9, A=H, B=(CH$_3$)$_3$CS, R$_{10}$=CH$_2$—CH$_3$);

6-(4-thio-tert-butoxyphenyl)-ethynyl nicotinic acid (Compound 10, A=H, B=(CH$_3$)$_3$CS, R$_{10}$=H);

ethyl 6-[4-(3-methyl-thio-2-butenoxyphenyl)]-ethynyl nicotinate (Compound 11, A=H, B=(CH$_3$)$_2$C=CH—CH$_2$—S—, R$_{10}$=CH$_2$—CH$_3$);

6-[4-(3-methyl-thio-2-butenoxyphenyl)]-ethynyl nicotinic acid (Compound 12, A=H, B=(CH$_3$)$_2$C=CH—CH$_2$—S—, R$_{10}$=H;

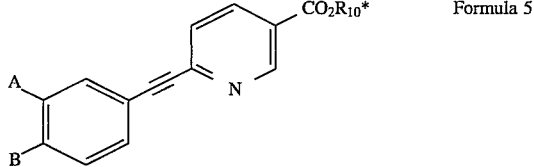

Formula 5

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, *Remington's Pharmaceutical Science*, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retionic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation Containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

The retionic acid like activity of these compounds was confirmed through the classic measure of retionic acid activity involving the effects of retionic acid on ornithine decarboxylase. The original work on the correlation between retionic acid and decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-0-tetradecanoyl-phorbol-13-acetate (TPA) induces ODC activity. Retionic acid inhibits this induction of ODC activity by TPA. The compounds of this invention also inhibit TPA induction of ODC as demonstrated by an assay essentially following the procedure set out in *Cancer Res.*, 35: 1662–1670, 1975.

By way of example of retinoic acid-like activity it is noted that in the assay conducted essentially in accordance with the method of Verma & Boutwell, ibid, the following examples of the preferred compounds of the present invention (Compounds 1, 3, 5, 6a, 6b, 7, 9 and 11) attained an 80% inhibition of TPA induced ODC activity at the following concentrations ($IC_{80}$):

| Compound | $IC_{80}$ conc (nmols) |
|---|---|
| 1 | 19.2 |
| 3 | 11.5 |
| 5 | –300 |
| 6a | 95 |
| 6b | 47 |
| 7 | 27.6 |
| 9 | 36.2 |
| 11 | 33.9 |

Specific Embodiments

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Referring now specifically to Reaction Scheme 1, the compounds of the invention can be synthesized by coupling of a suitable substituted phenylethyne compound (shown and defined in connection with Formula 2) with a suitable heterocyclic compound (shown and defined in connection with Formula 3) which has a leaving group (X in Formula 3). In other words, the heteroaryl substituent is coupled to the substituted phenylethyne compound (Formula 2) by reacting the latter with a halogen substituted heteroaromatic compound (Formula 3) in which the heteroaramatic nucleus (Y) either has the desired substituent E—Z or wherein the actual substituent E—Z' can be readily converted to the desired substituent by means of organic reactions well known in the art.

REACTION SCHEME I

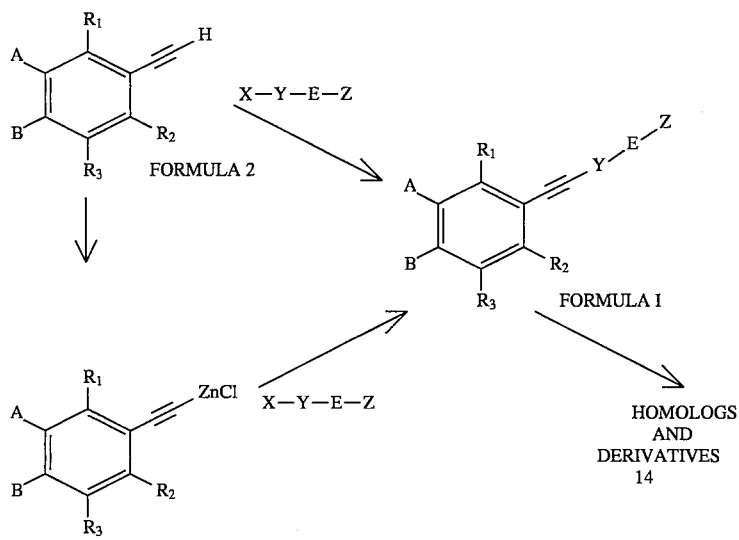

Coupling of the substituted phenylethyne compound (Formula 2) with the reagent X—Y—E—Z (Formula 3) or with the reagent X—Y—E—Z' (where Z' is defined as above in connection with Formula 4) is affected directly in the presence of cuprous iodide, a suitable catalyst, typically of the formula $pd(PQ_3)_2Cl_2$ and an acid acceptor, such as triethylamine, by heating in a sealed tube under an inert gas (argon) atmosphere.

The resulting disubstituted acetylene compounds may be the target compound made in accordance with the invention (Formula 1), or maybe compounds described by Formula 4 which can be readily converted into the target compounds by such steps as salt formation, esterification, deesterification, homologation, amide formation and the like. These steps are further discussed below.

The disubstituted acetylene compounds of the invention (Formula 1) may also be obtained by first converting the substituted phenylethyne compounds of Formula 2 into the corresponding metal salts, such as a zinc salt (Compound 13) and thereafter coupling the salt 13 with the reagent X—Y—E—Z (Formula 3) or with the reagent X—Y—E—Z' (Z' defined as above) in the presence of a catalyst having the formula $Pd(PQ_3)_4$ (Q is phenyl), or similar complex.

Derivatization of the compounds of Formula 1 (or of compounds of Formula 4) is indicated in Reaction Scheme 1 as conversion to "Homologs and Derivatives" (Compounds 14).

More specifically with respect to either derivatization or deblocking of protected functionalities in compounds corresponding to Formula 1 or Formula 4, or with respect to the preparation of heteroaromatic compounds of the formula X—Y—E—Z or of the formula X—Y—E—Z' (that is intermediates which after coupling either directly yield the compounds of the invention, or yield the compounds of Formula 4) the following is noted.

Where a protected heteroaromatic compound is needed to couple with the compounds of Formula 2 such may be prepared from their corresponding acids, alcohols, ketones or aldehydes. These starting materials, the protected acids, alcohols, aldehydes or ketones, are all available from chemical manufacturers or can be prepared by published methods.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before effecting a coupling reaction, where such compounds are not available from a commercial source, the heteroaromatics where Z is —COOH are subjected to homologation by successive treatment under Arndt-Eistert conditions or other homologation procedures. Alternatively, heteroaromatics where Z is different from COOH, may also be homologated by appropriate procedures. The homologated acids can then be esterified by the general procedure outlined in the preceding paragraph.

An alternative means for making compounds where n is 0–6 is to subject the compounds of Formula 1, where Z is an acid or other function, to homologation, using the Arndt-Eistert method referred to above, or other homologation procedures.

The acids and salts derived from Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert inorganic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkylhalides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds where Z is H can be prepared from the corresponding halo-heterocyclic entity, preferably where the halogen is iodine.

The intermediate substituted phenylethynes (compounds of Formula 2) can be prepared from substituted phenyl compounds in accordance with the reactions described below.

Alkyl, cycloalkyl or alkenyl substituted phenylethynes (compounds shown in Formula 2 where $R_1$–$R_3$ as well as A and B independently are hydrogen, lower alkyl, cycloalkyl, or lower alkenyl) can be synthesized in accordance with Reaction Scheme 2, starting from a halogen (preferably bromo or iodo) substituted phenyl compound (Compound 15). Compound 15 is reacted with trimethylsilylacetylene Compound 16 in the presence of cuprous iodide and a suitable catalyst, typically having the formula $Pd(PQ_3)_2Cl_2$ (Q is phenyl). The reaction is typically conducted in the presence of bis(triphenylphosphine)palladium (II) chloride catalyst, an acid acceptor, (such as triethylamine) under an inert gas (argon) atmosphere, by heating in a sealed tube. The resulting alkyl or alkenyl substituted trimethylsilylethynylbenzene is shown as Compound 17 in Reaction Scheme 2.

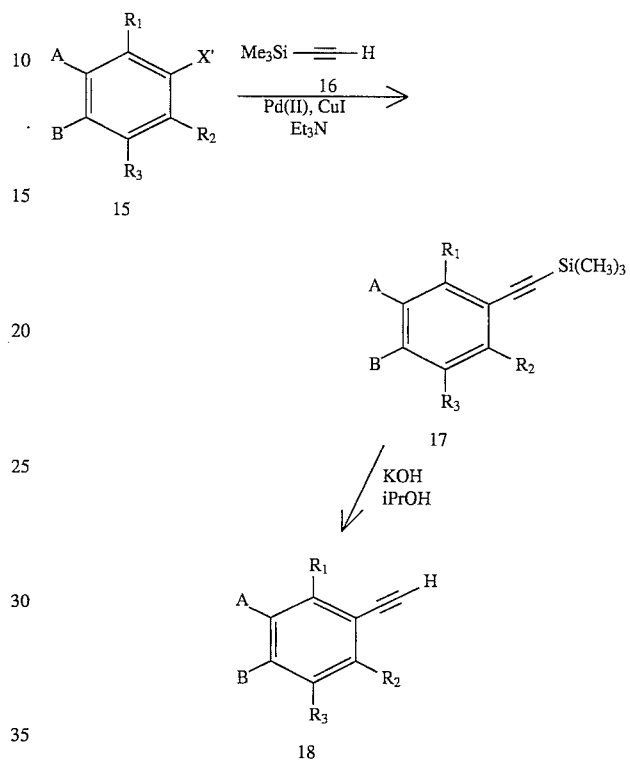

Reaction Scheme 2

As is shown on Reaction Scheme 2, the trimethylsilyl moiety is removed from the trimethylsilylethynylbenzene 17 in the next synthetic step, to provide the alkyl or alkenyl substituted ethynylbenzene derivative (Compound 18). The latter reaction is conducted under basic conditions, preferably under an inert gas atmosphere.

Reaction Scheme 3 discloses a specific synthetic route to 4-tert-butylphenyl ethyne (Compound 19) starting with 4-bromo t-butylbenzene (Compound 20) which is either available commercially or is readily synthesized in accordance with known prior art. Thus, 4-bromo t-butylbenzene 20 is heated with trimethylsilylacetylene 16 in the presence of cuprous iodide, bis(triphenylphosphine)palladium (II) chloride catalyst, and triethylamine under an inert gas atmosphere. The resulting trimethylsilyl-(4-tert-butyl)phenylethyne (Compound 21) is reacted with aqueous KOH in isopropanol to yield 4-tert-butylphenyl ethyne 19.

Reaction Scheme 3

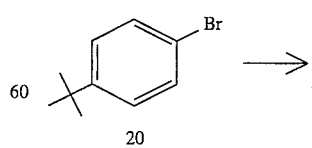

11
-continued
Reaction Scheme 3

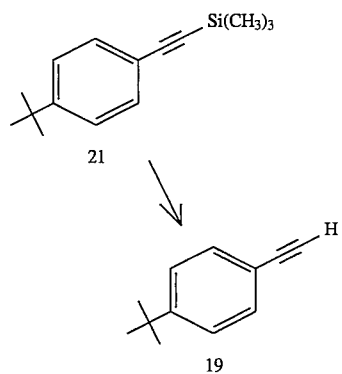

mobenzene (Compound 24). 3-Tert-butyl bromobenzene 24 is thereafter converted into the ethyne derivative 22 through the trimethylsilyl ethyne intermediate 25 in steps similar to the steps described in connection with Reaction Scheme 3.

Reaction Scheme 5 discloses a specific synthetic route to 4-(4-methylpentyl)-phenylethyne (Compound 26). In accordance with this scheme, bromobenzene (Compound 27) is reacted under Friedel Crafts conditions (AlCl$_3$) with the acid chloride (Compound 28) prepared in situ from 4-methyl valeric acid, to yield 4-(1-oxo-4-methyl-pentyl)bromobenzene (Compound 29). Compound 29 is reduced under Wolff-Kishner conditions (KOH, NH$_2$NH$_2$) to yield 4-(4-methylpentyl)bromobenzene (Compound 30). The bromobenzene derivative 30 is converted to the ethyne derivative 26 through the intermediate trimethylsilyl ethyne derivative 31 in a manner similar to the conversion described in connection with Reaction Scheme 3.

Reaction Scheme 4

Reaction Scheme 4 discloses a specific synthetic route to 3-tert-butylphenyl ethyne (Compound 22) starting with meta bromobenzoic acid (Compound 23), which is treated with trimethylaluminum in hexane to yield 3-tert-butyl bro- Reaction Scheme 5

-continued
Reaction Scheme 5

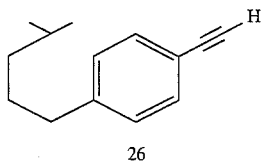

26

Reaction Scheme 6 discloses specific synthetic steps leading to 4-(1,1,4-trimethylpentyl)phenylethyne (Compound 32). In this synthetic route 4-(1-oxo-4-methyl-pentyl)bromobenzene (Compound 29, obtained as shown in Reaction Scheme 5) is reacted under a nitrogen atmosphere with trimethylaluminum in hexane to yield 4-(1,1,4-trimethylpentyl)bromobenzene (Compound 33). The bromobenzene derivative 33 is converted through the corresponding trimethylsilylethyne derivative 34 into the target intermediate 32 by treatment with trimethylsilyl ethyne and subsequently with KOH in isopropanol, as described above.

enoxy or thio-alkenoxy halobenzene (Compound 36) is reacted with trimethylsilylacetylene (Compound 16) in the presence of cuprous iodide and a suitable catalyst, such as $Pd(PQ_3)_2Cl_2$, where Q is phenyl. As is noted in connection with the analogous reaction disclosed in Reaction Scheme 2, the reaction is typically conducted in the presence of bis-(triphenylphosphine)palladium (II) chloride catalyst, and an acid acceptor, such as triethylamine, under an inert gas (argon) atmosphere. The resulting alkoxy, thio-alkoxy, alkenyloxy or thio-alkenyloxy trimethylsilylethynylbenzene derrivatives are shown as Compound 37 in Reaction Scheme 7.

Reaction Scheme 6

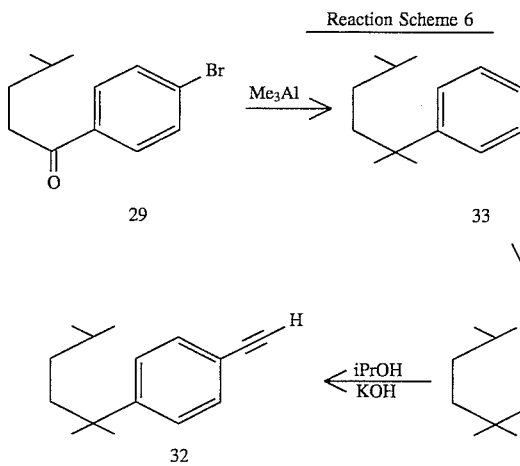

Specific examples of coupling the above-noted phelylethynes with reagents of the General Formula 3 are disclosed below under the heading "Specific Examples".

Alkylthio, alkyloxy, cycloalkylthio, cycloalkyloxy, alkenylthio, and alkenyloxy substituted phenylethynes which may or may not be additionally substituted with alkyl, cycloalkyl or alkenyl groups, in other words, compounds shown in Formula 2 where $R_1$–$R_3$ independently are hydrogen, lower alkyl, cycloalkyl, or lower alkenyl and where at least one of A and B is alkylthio, alkyloxy, cycloalkylthio, cycloalkyloxy, alkenylthio, or alkenyloxy, can be synthesized in accordance with the steps outlined in Reaction Scheme 7.

Thus, in accordance with Reaction Scheme 7 a halogen substituted phenol, preferably an iodopheol or a bromophenol, or a corresponding thiophenol (Compound 35) which may or may not be additionally substituted with an alkyl, alkenyl or cycloalkyl group (in Compound 35 X' is halogen, Y' is sulphur or oxygen and $R_1$–$R_3$ are defined as in connection with Formula 1) is alkylated with a reagent $R_4$—X" where X" is a leaving group such as a halogen, and $R_4$ is defined as in connection with Formula 1. Alternatively, the $R_4$ group can also be formed by reacting the halogen substituted thiophenol or phenol (Compound 35) with an appropriate alkene. The resulting alkoxy, thio-alkoxy, alk- Reaction Scheme 7

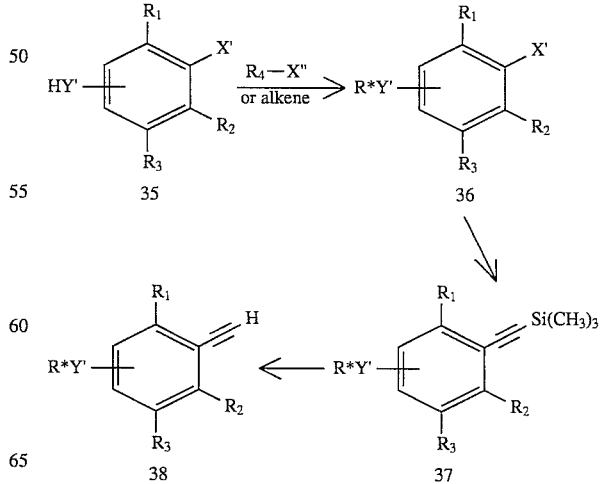

The trimethylsilyl moiety is removed from the trimethylsilylethynylbenzene 37 in the next synthetic step, to provide the alkoxy, thio-alkoxy, alkenoxy or thio-alkenoxy substituted ethynylbenzene derivative (Compound 38).

Reaction Scheme 8

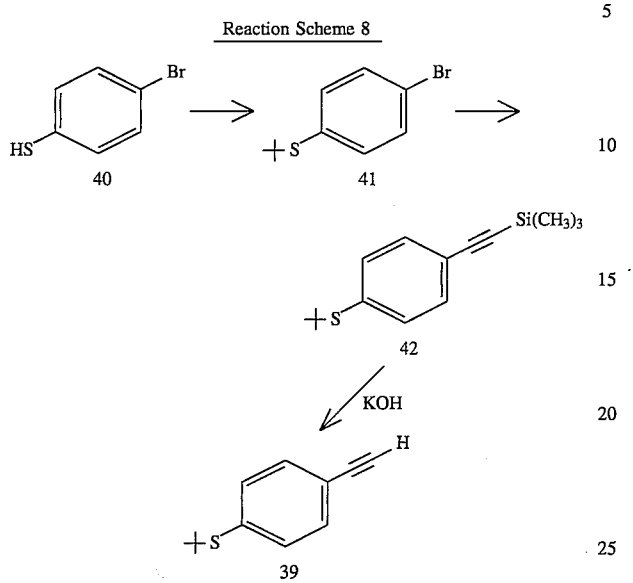

Reaction Scheme 8 discloses a specific series of synthetic steps which lead to 4-thio-tert-butoxyphenyl ethyne (Compound 39). Thus, 4-bromo-thiophenol (Compound 40) is reacted with isobutylene gas to yield 4-bromophenyl-tert-butyl-sulfide (Compound 41). Compound 41 is thereafter reacted under the conditions described above, with trimethylsilylacetylene (Compound 16) and the resulting trimethylsilyl phenylethyne derivative 42 is thereafter hydrolyzed to yield Compound 39. The corresponding 3-thio-tert-butoxyphenyl ethyne (Compound 43) can be synthesized from 3-bromo-thiophenol under substantially similar conditions.

4-bromo-2-methyl-2-butene (Compound 45) in a suitable solvent (such as acetone) in the presence of strong base (NaOH) to yield 4-bromophenyl-3-methyl-2-butenyl-sulfide (Compound 46). Compound 46 is converted to the ethyne derivative 44 through the trimethylsilyl ethyne compound 47 by the reactions which are described above.

Reaction Scheme 9

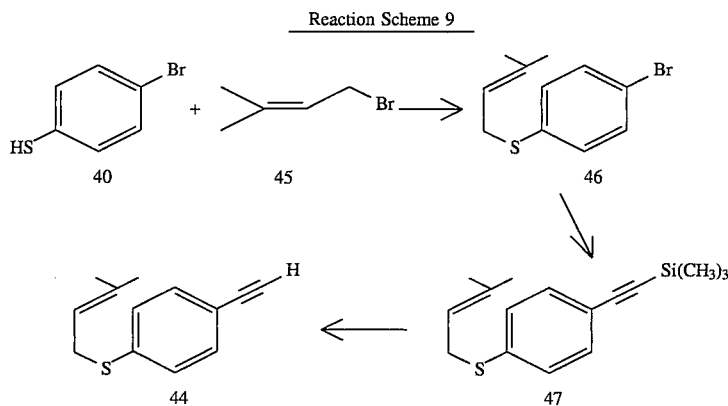

Reaction Scheme 9 discloses synthetic steps which lead to 4-(3-methyl-thio-2-butenoxy)phenyl ethyne (Compound 44). 4-Bromo-thiophenol (Compound 40) is heated with

Reaction Scheme 10

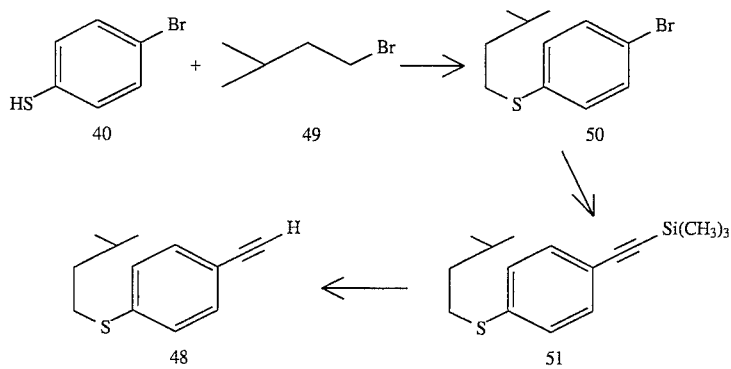

Reaction Scheme 10 illustrates specific synthetic steps which can be utilized to obtain 4-(3-methyl-thiobutoxy)-phenyl ethyne (Compound 48). In this synthetic procedure 4-bromothiophenol (Compound 40) is heated with 1-bromo-3-methyl-2-butane (Compound 49) in a suitable solvent in the presence of strong base (refluxing acetone and NaOH) to yield 4-bromophenyl-3-methylbutyl-sulfide (Compound 50). Compound 50 is transformed to the desired ethyne derivative 48 through the intermediate trimethylsilylethyne 51.

Reaction Scheme 11

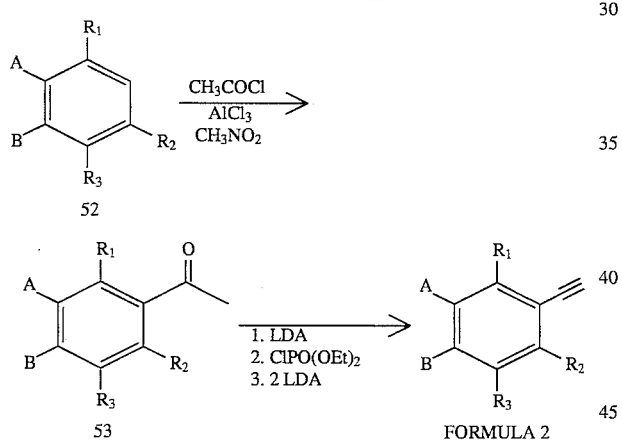

An alternative general route for introducing the ethyne (acetylenic) function into a phenyl or substituted phenyl derivative so as to obtain the intermediates of Formula 2, is disclosed in Reaction Scheme 11. In accordance with this general procedure, a suitably substituted benzene derivative (Compound 52) is acetylated under Friedel Crafts conditions to provide the acetophenone derivative 53. The acetylation is preferably conducted in the presence of $AlCl_3$ and in nitromethane solvent. The acetylenic (triple) bond is introduced into the molecule by converting the acetyl moiety of the acetophenone derivative 53 to an acetylene moiety. This is accomplished, preferably, by treatment with lithium diisopropylamide (at low temperature, such as −78 degrees C.) which causes enolization of the acetyl group. The intermediate enol compound (not shown in Reaction Scheme 11) is esterified by treatment with diethylchlorophosphate (or the like) and is again reacted at reduced temperature (e.g. −78 degrees C.) with two equivalents of lithium diisopropylamide, to form the triple bond (presumably by an elimination reaction) and to yield the compounds of Formula 2.

It is noted at this point that the present invention is not intended to be limited or bound by the above-mentioned and other theories of reaction mechanisms. Brief description of the theories of reaction mechanism of the above-noted reaction is given to further enable and facilitate the work of a skilled artisan in the field to modify and adjust the synthetic conditions to fit particular specific intermediates and to make the several compounds of the invention, without departing from the scope and spirit of the invention.

The following examples of specific compounds of the invention, and specific examples of the synthetic steps in which the compounds and certain intermediates are made, are set out to illustrate the invention, not to limit its scope.

SPECIFIC EXAMPLES

Ethyl 6-chloronicotinate (Compound 54)

A mixture of 15.75 g (0.1 mol) 6-chloronicotinic acid, 6.9 g (0.15 mol) ethanol, 22.7 g (0.11 mol) dicyclohexylcarbodiimide and 3.7 g dimethylaminopyridine in 200 ml methylene chloride was heated at reflux for 2 hours. The mixture was allowed to cool, solvent removed in vacuo and residue subjected to flash chromatography to give the title compound as a low-melting white solid. PMR ($CDCl_3$): & 1.44 (3H, t, J-6.2 Hz) 4.44 (2H, q, J-4.4 Hz), 7.44 (1H, d, J-8.1 Hz), 8.27 (1H, dd, J-8.1 Hz, 3 Hz), 9.02 (1H, d, J-3 Hz).

The foregoing procedure may be used to esterify any of the other halo-substituted acids employed in the making of compounds of the invention, such as:

ethyl 2-(2-chloropyrid-5-yl)acetate;
ethyl 5-(2-chloropyrid-5-yl)pentanoate;
ethyl 2-(2-iodofur-5-yl)acetate;
ethyl 5-(2-iodofur-5-yl)pentanoate;
ethyl 2-(2-iodothien-5-yl)acetate;
ethyl 5-(2-iodothien-5-yl)pentanoate;
ethyl 2-(3-chloropyridazin-6-yl)acetate;
ethyl 5-(3-chloropyridazin-6-yl)pentanoate; and the corresponding chloro, or other halo, substituted pyrimidinyl or pyrazinyl analogues of such esters. The just mentioned esters (including ethyl-6-chloronicotinate, Compound 54) can serve as the reagents, X—Y—E—Z for coupling with the correspoding ethynyl compounds (such as Compounds 19, 22, 26, 32, 39, 44, and 48, or their zinc salts) to provide the target compounds of the invention.

3-Tert-butyl bromobenzene (Compound 24)

A suspension of 4.02 g (20 mmol) of m-bromobenzoic acid (Compound 23) in 10 ml hexane was cooled in an ice-bath under nitrogen and then treated slowly with 40 ml of 2M (80 mmol) trimethylaluminum in hexane. The hexane was removed by distillation under nitrogen and the apparatus modified for reflux. The reaction mixture was then heated in an oil bath at 140–150 degrees C. for 3 hours. The oil bath was then replaced by an ice-water bath and the reaction mixture was quenched by the slow dropwise addition of water. The mixture was acidified with dilute HCl and mixture heated at reflux until the aluminum salts were dissolved. The reaction mixture was allowed to cool and extracted with 3×8 ml ether. The ether extracts were combined, washed with dil. HCl, water and saturated NaCl and then dried (MgSO$_4$). The solvent was removed in-vacuo and the residue distilled to give a mixture of the title compound and 3-(1-methyl-ethenyl)bromobenzene as a colorless oil. A small portion (200 mg) of this mixture was dissolved in 1 ml of methylene chloride and then treated with a solution of 200 mg of m-chloroperbenzoic acid in 4 ml of methylene chloride. The mixture was stirred at room temperature for 1 hour and the methylene chloride removed in-vacuo. The residue was dissolved in hexane and filtered through a short silica column and the filtrate concentrated in-vacuo to give pure title compound as a colorless oil. PMR (CDCl$_3$): & 1.30 (9H, s), 7.25 (1H, m), 7.41 (2H, m), 7.65 (H, t, J-2.1 Hz).

4-(1-oxo-4-methyl-pentyl)bromobenzene (Compound 29)

A mixture of 25 g (0.215 mol) of 4-methyl varleric acid and 29.35 g (0.247 mol) of thionyl chloride was heated at reflux for 1.5 hour. The excess thionyl chloride was removed under reduced pressure using a cryogenic trap. The residue was taken up with 120 g (0.764 mol) of bromobenzene (Compound 27) and the mixture was cooled in an ice-bath and then treated with 23 g (0.172 mol) of anhydrous aluminum chloride through a powder addition funnel. The mixture was stirred at room temperature for 82 h and then quenched by the addition of 50 ml of an ice/water mixture, followed by 30 ml of conc. HCl. The organic layer was separated and the aqueous layer extracted with 2×50 ml of ether. The organic extracts were combined and washed successively with water and saturated NaCl solution and then dried (MgSO$_4$). The solvent was then removed in-vacuo and the residue purified by distillation (–80 degrees C./0.01 mm) to give the title compound as a colorless solid. PMR (CDCl$_3$): & 0.94 (6 H, d, J-6.0 Hz), 1.53–1.68 (3H, m), 2.85–2.97 (2H, m)., 7.60 (2H, d, J-8.4 Hz), 7.83 (2H, d, J-8.4 Hz).

4-(4-methylpentyl)bromobenzene (Compound 30)

A mixture of 6.45 g (115 mmol) of potassium hydroxide and 42 ml of triethylene glycol was heated at around 100 degrees C. until the potassium hydroxide was dissolved. The mixture was allowed to cool and then treated with 10 g (39 mmol) of 4-(1 -oxo-4-methylpentyl)bromobenzene (Compound 29) followed by 3 g (94 mmol) of hydrazine hydrate. The mixture was slowly brought to reflux and heated at reflux for 1 hour. The apparatus Was modified for distillation and the mixture heated until approximately 7 ml of liquid had distilled over and the flask temperature had reached 220 degrees C. The apparatus was again modified for reflux and the mixture was heated at reflux for 5 hours and then stirred at room temperature for 8.5 hours. The mixture was then heated to 100 degrees C. and poured into 40 ml of water and the flask rinsed with an additional 25 ml of water. This diluted mixture was acidified to pH=2 with conc. HCl and extracted with ether. The ether extract was washed successively with water and saturated NaCl and then dried (MgSO$_4$). The solvent was removed in vacuo and the residue subjected to kugelrohr distillation (70 degrees C., 0.05 mm) to give the title compound as a colorless oil. PMR (CDCl$_3$): & 0.88 (6H, d, J-6 Hz), 1.12–1.26 (2H, m), 1.48–1.66 (3H, m), 2.54 (2H, t, J-7.7 Hz) 7.06 (2H, d, J-8.3 Hz), 7.39 (2H, d, J-8.3 Hz).

4-(1,1,4-Trimethyl-pentyl)bromobenzene (Compound 33)

To a cooled (ice bath) solution of 5.35 g (20.9 mmol) of 4-(1-oxo-4-methylpentyl)bromobenzene (Compound 29) and 200 ml of water in 8 ml of chlorobenzene was added slowly, under nitrogen, 20.9 ml of 2M (41.8 mmol) trimethylaluminum in hexane. The hexane was removed by distillation under nitrogen and the residue heated at reflux for 80 hours. The reaction mixture was then cooled in an ice bath and quenched by the slow addition of water. The mixture was then treated with 24 ml of 2N HCl and heated until the aluminum salts were dissolved. The mixture was cooled and extracted with 3×20 ml of ether. The ether extracts were combined and washed successively with water and saturated NaCl and then dried (MgSO$_4$). The solvent was removed in-vacuo and the residue distilled (90–100 degrees C./0.16 mm) to give a crude product which appeared to be a mixture of the desired title compound, starting bromoketone and some olefinic material. This product was then dissolved in 20 ml of methylene chloride, treated with 2 g of m-chloroperbenzoic acid and stirred at room temperature for 12 hours. The solvent was then removed in-vacuo and the residue purified by flash chromatography (silica, hexane) to give the title compound as a colorless oil PMR (CDCl$_3$): & 0.82 (6H, d, J-6.9 Hz), 0.85–0.97 (2H, m), 1.27 (6H, s), 1.32–1.49 (1H, m), 1.53–1.62 (2H, m), 7.20 (2H, d, J-8.7 Hz), 7.42 (2H, d, J-8.7 Hz).

Trimethylsilyl(4-tert-butyl)phenylethyne (Compound 21)

A stirred mixture of 3.05 g (14.31 mmol) of 4-tert-butyl-bromobenzene (Compound 20), 1.41 g (14.39 mmol) of trimethylsilylacetylene (Compound 16), 139 mg (0.13 mmol) of cuprous iodide, 293 mg (0.42 mmol) of bis(triphenyophosphine)palladium (II) chloride and 3 ml of triethylamine was flushed with nitrogen and then heated under nitrogen at 65–70 degrees C. for 20 hours. The reaction mixture was stirred at room temperature for a further 4 hours and the triethylamine then removed under vacuum. The residue was purified by flash chromatography (silica; hexanes) to give the title compound as a colorless oil. PMR (CDCl$_3$): & 0.26 (9H, s), 1.31 (9H, s), 7.32 (2H, d, J-8.2 Hz), 7.42 (2H, d, J-8.2 Hz).

Trimethylsilyl(3-tert-butyl)phenylethyne (Compound 25)

Using the same general procedure as described for Compound 21, but using 3-tert-butyl-bromobenzene, (Compound 24) the title compound was synthesized as a colorless oil. PMR (CDCl$_3$): & 0.36 (9H, s), 1.40 (9H, s), 7.32 (1H, m), 7.37–7.47 (2H, m), 7.61 (1H, m).

Trimethylsilyl[4-(4-methylpentyl)]phenylethyne (Compound 31)

Using the same general procedure as described for Compound 21, but using instead 4-(4-methylpentyl)bromobenzene (Compound 30), the title compound was synthesized as a colorless oil. PMR (CDCl$_3$): & 0.32 (9H, s), 0.93 (6H, d, J-6.6 Hz), 1.18–1.29 (2H, m), 1.52–1.70 (3H, m), 2.58 (2H, t, J-7.7 Hz), 7.12 (2H, d, J-8.1 Hz), 7.43 (2H, d, J-8.1 Hz).

Trimethylsilyl[4-(1,1,4-trimethylpentyl)]phenylethyne (Compound 34)

Using the same general procedure as described for Compound 21, but using instead 4-(1,1,4-trimethylpentyl)bromobenzene (Compound 33), the title compound was synthesized as a colorless oil. PMR (CDCl$_3$): & 0.26 (9H, s), 0.81 (6H, d, J-6.6 Hz), 0.85–0.97 (2H, m), 1.29 (6H, s), 1.33–1.46 (1H, m), 1.54–2.65 (2H, m), 7.27 (2H, d, J-8.1 Hz), 7.42 (2H, d, J-8.1 Hz).

(4-tert-butyl)phenylethyne (Compound 19)

To a stirred solution of 1.44 g (6.23 mmol) of trimethylsilyl(4-tert-butyl)phenylethyne (Compound 21) in 5 ml of isopropanol was added 10 ml of 1N aqueous KOH and the mixture then stirred at room temperature for 6.5 hours. The isopropanol was removed under vacuum and the residue extracted with ether. The ether extract was washed with dilute HCl until the washings were acidic. The ether solution was then successively washed with water, saturated NaCl and NaHCO$_3$ solutions and then dried (MgSO$_4$). Solvent was then removed in-vacuo to give the title compound as a colorless oil. PMR (CDCl$_3$): & 1.34 (9H, s), 3.05 (1H, s), 7.37 (2H, d, J-8.2 Hz), 7.46 (2H, d, J-8.2 Hz).

(3-tert-butyl)phenylethyne (Compound 22)

Using the same general procedure as described for Compound 19, but using instead trimethylsilyl(3-tert-butyl)phenylethyne (Compound 25) and aqueous KOH in methanol, the title compound was synthesized as a colorless oil. PMR (CDCl$_3$): & 1.29 (9H, s), 3.03 (1H, s), 7.22 (1H, t, J-7.5 Hz), 7.30 (1H, dt, J-7.5 Hz, 1.5 Hz), 7.36 (1H, dt, J-7.5 Hz, 1.5 Hz), 7.53 (1H, t, J-1.5 Hz).

[4-(4-methylpentyl)]phenylethyne (Compound 26)

Using the same general procedure as described for Compound 19, but using instead trimethylsilyl[4-(4-methylpentyl)] phenylethyne (Compound 31), the title compound was synthesized as a colorless oil. PMR (CDCl$_3$): & 0.94 (6H, d, J-6.6 Hz), 1.20–1.32 (2H, m), 1.56–1.62 (3H, m), 2.64 (2H, t, J-7.8 Hz), 3.08 (1H, s), 7.18 (2H, d, J-8.1 Hz), 7.47 (2H, d, J-8.1 Hz).

[4-(1,1,4-trimethylpentyl)]phenylethyne (Compound 32)

Using the same general procedure as described for Compound 19, but using instead trimethylsilyl[4-(1,1,4-trimethylpentyl)] phenylethyne (Compound 34), the title compound was synthesized as a colorless oil. PMR (CDCl$_3$): & 0.81 (6H, d, J-6.6 Hz), 0.85–0.96 (2H, m), 1.29 (6H, s), 1.32–1.48 (1H, m). 1.55–1.66 (2H, m)., 3.04 (1H, s), 7.29 (2H, d, J-8.4 Hz), 7.44 (2H, d, J-8.4 Hz).

Ethyl-6-(4-tert-butylphenylethynyl)nicotinate (Compound 3)

A mixture of 477.7 mg (3.02 mmol) of 4-tertbutylphenylethyne (Compound 19), 556.5 mg (3.01 mmol) of ethyl-6-chloronicotinate (Compound 54), 27.8 mg (0.15 mmol) of cuprous iodide, 58.7 mg (0.08 mmol) of bis(triphenylphosphine)palladium (II) chloride and 2 ml of triethylamine was degassed under nitrogen and then stirred under nitrogen at room temperature for 40 hours. The mixture was then heated at 65 degrees C. for 12 hours, cooled to room temperature and the excess triethylamine removed under vacuum. The residue was taken up in water and extracted with ether. The solvent was then removed in-vacuo and the residue purified by flash chromatography (silica 5% ethyl acetate in hexane) to give the title compound as a pale brown solid. PMR (CDCl$_3$) : & 1.33 (9H, s), 1.42 (3H, t, J-7.1 Hz); 4.42 (2H, q, J-7.1 Hz), 7.40 (2H, d, J-8.4 Hz), 7.53–7.61 (3H, m), 8.28 (1H, dd, J-8.1 Hz, 2.0 Hz), 9.20 (1H, d, J-2.0 Hz).

Ethyl-6-(3-tert-butylphenylethynyl)nicotinate (Compound 1)

Using the same general procedure as described for Compound 3, but using instead 3-tert-butylphenylethyne (Compound 19), the title compound was synthesized as a white solid. PMR (CDCl$_3$): & 1.34 (9H, s), 1.42 (3H, t, J-7.2 Hz), 4.43 (2H, q, J-7.2 Hz), 7.28–7.36 (1H, m), 7.40–7.46 (2H, m), 7.60 (1H, d, J-8.1 Hz), 7.67 (1H, s), 8.29 (1H, dd, J-8.1 Hz, 2.1 Hz), 9.21 (1H, d, J-2.1 Hz).

Ethyl-6-[4-(4-methylpentyl)phenylethynyl]nicotinate (Compound 5)

Using the same general procedure as described for Compound 3, but using instead 4-(4-methylpentyl)phenylethyne (Compound 26), the title compound was synthesized as a yellow solid. PMR (CDCl$_3$): & 0.91 (6 H, d, J-6.6 Hz), 1.20–1.30 (1H, m)., 1.47 (3H, t, J-7.2 Hz), 1.51–1.72 (3H, m), 2.63 (2H, t, J-7.8 Hz), 4.45 (2H, q, J-7.2 Hz), 7.22 (2H, d, J-8.4 Hz), 7.53–7.64 (3H, m), 8.30 (1H, dd, J-8.1 Hz, 2.1 Hz), 9.23 (1H, d, J-2.1 Hz).

Ethyl 6-4-(1,1,4-trimethylpentyl)phenylethynyl]nicotinate (Compound 6a)

Using the same general procedure as described for Compound 3, but using instead [4-(1,1,4-trimethylpentyl)]phenylethyne (Compound 32), the title compound was synthesized as a yellow oil. PMR (CDCl$_3$): & 0.83 (6H, d, J-6.7 Hz), 0.88–0.99 (2H, m), 1.32 (6H, s), 1.35–1.50 (4H, m), 1.59–1.70 (2H, m), 4.45 (2H, q, J-7.1 Hz), 7.36 (2H, d, J-8.4 Hz), 7.55–7.64 (3H, m), 8.30 (1H, dd, J-8.0 Hz, 2.2 Hz), 9.23 (1H, d, J-2.2 Hz).

6-(3-Tert-butylphenylethynyl)nicotinic acid (Compound 2)

A solution of 60 mg (0.195 mmol) of ethyl 6-(3-tert-butylphenylethynyl)nicotinate (Compound 1) in 4 ml of aqueous ethanolic KOH was stirred at room temperature for 24 hours. The mixture was concentrated in-vacuo and the residue was treated with 5 ml of water and 5 ml of ether. The aqueous layer was separated and washed with a further 5 ml of ether. The aqueous layer was then acidified with 3 ml of 10 percent HCl and extracted with 2×5 ml of ether. The ether extracts were combined and washed with saturated NaCl solution and then dried (MgSO$_4$). The solution was concentrated in-vacuo to give the title compound as a pale yellow solid. PMR (CDCl$_3$): & 1.26 (9H, s), 7.25 (1H, t, J-7.8 Hz), 7.35–7.42 (2H, m), 7.56–7.63 (2H, m), 8.35 (1H, dd, J-8.2 H, 2.1 Hz), 9.31 (1H, d, J-2.1 Hz).

4-Bromophenyl-tert-butyl-sulfide (Compound 41)

A constant flow of isobutylene was bubbled through a solution of 4 g (21.16 mmol) of 4-bromo-thiophenol (Compound 40) in 250 ml of methylene chloride under a nitrogen atmosphere and the mixture treated slowly with 0.6 ml of conc. H$_2$SO$_4$. Isobutylene was bubbled through the reaction mixture at room temperature for 2.5 hours and the mixture then stirred for a further 12 hours. The mixture was then washed successively with saturated NaHCO$_3$, water, 1N HCl, water and saturated NaCl and then dried (MgSO$_4$). The solvent was then removed in-vacuo and the residue purified by flash chromatography (silica; 3% ethyl acetate in hexanes) to give the title compound as a colorless oil. PMR (CDCl$_3$): & 1.28 (9H, s), 7.39 (2H, d, J-8.4 Hz), 7.47 (2H, d, J-8.4 Hz).

3-Bromophenyl tert-butyl sulfide (Compound 55)

Isobutylene was bubbled through 75% H$_2$SO$_4$ solution at −5 degrees C. until 2.65 g (47.2 mmol) of isobutylene had been absorbed. The mixture was treated with 3.8 g (20.1 mmol) of 3-bromothiophenol and then allowed to warm to room temperature and stirred for 72 hours. The reaction mixture was then poured into 40 ml of an ice/water mixture and then extracted with ether. The ether extracts were combined and washed successively with 5% NaOH, water and saturated NaCl solution and then dried (MgSO$_4$). The solvent was removed in-vacuo and the residue distilled (69–75 degrees C., 0.6mm) to give the title compound as a pale yellow oil. PMR (CDCl$_3$) : & 1.30 (9H, s), 7.23 (1H, t, J-8.0 Hz), 7.45–7.54 (2H, m) , 7.72 (1H, t, J-1.8 Hz).

4-Bromophenyl 3-methyl-2-butenyl sulfide (Compound 46)

A mixture of 12.8 g (67.7 mmol) of 4-bromothiophenol (Compound 40) and 2.7 g (67.7 mmol) of sodium hydroxide in 50 ml acetone was heated at reflux under argon for 2.5 hours. The refluxing mixture was then treated dropwise with a solution of 10.0 g (67.1 mmol) of 4-bromo-2-methyl-2-butene (Compound 45) in 10 ml acetone and the mixture heated at reflux for a further 24 hours. The mixture was then cooled and solvent removed in-vacuo. The residue was treated with 50 ml water and extracted with 3×75 ml ether. The ether extracts were combined and washed successively with 3×30 ml of 5% NaOH, 50 ml of water and 50 ml of saturated NaCl and then dried (MgSO$_4$). Solvent was then removed in-vacuo and the residual oil purified by kugelrohr distillation (70 degrees C., 0.1 mm) to give the title compound as a colourless oil. PMR (CDCl$_3$): & 1.58 (3H, s), 1.70 (3H, s) 3.5 (2H, d, J-7.0 Hz), 5.27 (1H, t, J-7.0 Hz), 7.17 (2H, d, J-8.3 Hz), 7.36 (2H, d, J-8.3 Hz).

4-Bromophenyl 3-methylbutyl sulfide (Compound 50)

A mixture of 15 g (79 mmol) of 4-bromo-thiophenol (Compound 40), 3.16 g (79 mmol) of powdered sodium hydroxide and 150 ml of acetone was heated at reflux for 15 minutes. The refluxing mixture was then treated dropwise with a solution of 12 g (79 mmol) of 1-bromo-3-methylbutane (Compound 49) in 25 ml of acetone and then refluxed for a further 18 hours. The mixture was allowed to cool and the solvent removed in-vacuo. The residue was taken up in 25 ml of water and the mixture basified with 2N NaOH solution. The mixture was extracted with ether and the combined ether extracts washed successively with 1N NaOH, water and saturated NaCl and then dried (MgSO$_4$). The solvent was removed in-vacuo and the residue distilled (113–117 degrees C., 0.2 mm) to give the title compound as a colourless oil. PMR (CDCl$_3$): & 0.93 (6H, d, J-6.6 Hz), 1.47–1.58 (2H, m), 1.65–1.80 (1H, m), 2.90 (2H, t, J-7.8 Hz), 7.18 (2H, d, J-8.6 Hz), 7.39 (2H, d, J-8.6 Hz).

Trimethylsilyl(4-thio-tert-butoxyphenyl)ethyne (Compound 42)

A mixture of 1.25 g (5.1 mmol) of 4-bromophenyl tert-butyl sulfide (Compound 41), 500 mg (5.1 mmol) of trimethylsilyl acetylene (Compound 16), 100 mg (0.53 mmol) of cuprous iodide, 200 mg (0.28 mmol) of bis(triphenylphosphine)palladium (II) chloride and 1 ml of triethylamine was degassed and then heated under argon at 55 degrees C. for 160 hours. The triethylamine was then removed under vacuum and the residue purified by flash chromatography (silica; hexanes) to give the title compound as a colourless oil. PMR (CDCl$_3$): & 0.20 (9H, s), 1.22 (9H, s), 7.32–7.42 (4H, AB quartet)

Trimethylsilyl(3-thio-tert-butoxyphenyl)ethyne (Compound 56)

Using the same general procedure as described for Compound 42, but using instead 3-bromophenyl tert-butyl sulfide (Compound 55), the title compound was synthesized as a pale yellow oil. PMR (CDCl$_3$): & 0.25 (9H, s), 1.25 (9H, s), 7.22 (1H, t, J-8.0 Hz), 7.39–7.46 (2H, m), 7.62 (1H, s).

Trimethylsilyl[4-[3-methyl-thio-2-butenoxyl)phenyl]ethyne (Compound 47)

Using the same general procedure as described for Compound 42, but using instead 4-bromophenyl 3-methyl-2-butenyl sulfide (Compound 46), the title compound was synthesized as a pale yellow oil. PMR (CDCl$_3$): & 0.25 (9H, s), 1.62 (3H, s), 1.71 (3H, s), 3.55 (2H, d, J-7.5 Hz), 5.28 (1H, t, J-7.5 Hz), 7.21 (2H, d, J-8.1 Hz), 7.36 (2H, d, J-8.1 Hz).

Trimethylsilyl[4-(3-methyl-thiobutoxy)phenyl]ethyne (Compound 51)

Using the same general procedure, as described for Compound 42, but using instead 4-bromophenyl 3-methyl-butyl sulfide (Compound 50), the title compound was synthesized as a colourless oil. PMR (CDCl$_3$): & 0.25 (9H, s), 0.92 (6H, d, J-6.6 Hz), 1.48–1.58 (2H, m), 1.65–1.79 (1H, m), 2.92 (2H, t, J-7.8 Hz), 7.20 (2H, d, J-8.4 Hz), 7.37 (2H, d, J-8.4 Hz).

4-Thio-tert-butoxyphenyl ethyne (Compound 39)

To a solution of 850 mg (3.24 mmol) of trimethylsilyl 4-thio-tert-butoxyphenylethyne (Compound 42) in 3 ml of isopropanol was added 5 ml of 1N KOH solution and the mixture was stirred at room temperature for 16 hours. The mixture was extracted with ether and the combined ether extracts were washed successively with dilute HCl, water, saturated NaHCO$_3$ and NaCl solutions and then dried (MgSO$_4$). The solvent was removed in-vacuo to give the title compound as a pale yellow oil. PMR (CDCl$_3$): & 1.29 (9H, s), 3.16 (1H, s), 7.42–7.52 (4H, AB quartet).

3-Thio-tert-butoxyphenyl ethyne (Compound 43)

Using the same general procedure as described for Compound 39, but using instead trimethylsilyl 3-thio-tert-butoxyphenyl ethyne (Compound 56), the title compound was synthesized as a colorless oil. PMR (CDCl$_3$): & 1.30 (9H, s), 3.11 (1H, s), 7.31 (1H, t, J-7.7 Hz), 7.48–7.56 (2H,m), 7.69 (1H, t, J-1.7 Hz).

4-(3-Methyl-thio-2-butenoxy)phenyl ethyne (Compound 44)

Using the same general procedure as described for Compound 39), but using instead trimethylsilyl 4-(3-methylthio-2-butenoxy)phenyl ethyne (Compound 47), the title compound was synthesized as a pale yellow oil. PMR (CDCl$_3$): & 1.63 (3H, s), 1.72 (3H, s), 3.08 (1H, s), 3.56 (2H, d, J-7.5 Hz), 5.29 (1H, t, J-7.5 Hz), 7.23 (2H, d, J-8.4 Hz), 7.38 (2H, d, J-8.4 Hz).

4-(3-methyl-thiobutoxy)phenyl ethyne (Compound 48)

Using the same general procedure as described for Compound 39, but using instead trimethylsilyl 4-(3-methylthiobutoxy)phenyl ethyne (Compound 51) the title compound was synthesized as a colourless oil. PMR (CDCl$_3$): & 0.93 (6H, d, J-6.7 Hz), 1.49–1.60 (2H, m), 1.65–1.80 (1H, m), 2.93 (2H, t, J-7.8 Hz), 7.22 (2H, d, J-8.5 Hz), 7.39 (2H, d, J-8.5 Hz).

Ethyl 6-(3-thio-tert-butoxyphenyl)ethynyl nicotinate (Compound 7)

A mixture of 198 mg (1.04 mmol) of 3-thio-tert-butoxyphenyl ethyne (Compound 43), 193 mg (1.04 mmol) of ethyl 6-chloro-nicotinate (Compound 54), 10 mg (0.05 mmol) of cuprous iodide, 20 mg (0.03 mmol) of bis(triphenylphosphine)palladium (II) chloride and 0.5 ml of triethylamine was degassed under nitrogen and heated at 55–60 degrees C. for 40 hours. The triethylamine was removed under vacuum and the residue purified by flash chromatography (silica, 10% ethyl acetate in hexanes) to give the title compound as a pale brown solid. PMR (CDCl$_3$): & 1.31 (9H, s), 1.43 (3H, t, J-7.2 Hz), 4.43 (2H, q, J-7.2 Hz), 7.36 (1H, t, J-7.8 Hz), 7.55–7.66 (3H, m), 7.81 (1H, t, J-1.7 Hz), 8.31 (1H, dd, J-8.2 Hz, 2.2 Hz), 9.22 (1H, d, J-2.2 Hz).

Ethyl 6-(4-thio-tert-butoxyphenyl)ethynyl nicotinate (Compound 9)

Using the same general procedure as described for Compound 7, but using instead 4-thio-tert-butoxyphenyl ethyne (Compound 39), the title compound was synthesized as a pale brown solid. PMR (CDCl$_3$): & 1.31 (9H, s), 1.43 (3H, t, J-7.1 Hz), 4.43 (2H, q, J-7.1 Hz), 7.51–7.63 (5H, m), 8.30 (1H, dd, J-8.1 Hz, 2.1 Hz), 9.22 (1H, d, J-2.1 Hz).

Ethyl 6-(4-(3-methyl-thiobutoxy)phenyl]ethynyl nicotinate (Compound 57)

Using the same general procedure as described for Compound 7, but using instead 4-(3-methyl-thiobutoxy)phenyl ethyne (Compound 48), the title compound was synthesized as a brown solid. PMR (CDCl$_3$): & 0.93 (6H, d, J-6.5 Hz) 1.42 (3H, t, J-7.1 Hz), 1.53–1.62 (2H, m), 1.67–1.82 (1H, m), 2.93–3.00 (2H, m)., 7.26 (2H, d, J-8.4 Hz), 7.52 (2H, d, J-8.4 Hz), 7.58 (1H, d, J-8.2 Hz) 8.29 (1H, dd, J-8.2 Hz, 2.1 Hz), 9.20 (1H, d, J-2.1 Hz).

Ethyl-6-[4-(3-methyl-thio-2-butenoxy)phenyl]ethynyl nicotinate (Compound 11)

Using the same general procedure as described for Compound 7, but using instead 4-(3-methyl-thio-2-butenoxy)phenyl ethyne (Compound 44), the title compound was synthesized as a pale yellow solid. PMR (CDCl$_3$): & 1.43 (3H, t, J-7.1 Hz), 1.66 (3H, s), 1.74 (3H, s), 3.59 (2H, d, J-7.5 Hz), 4.43 (2H, q, J-7.1 Hz), 5.31 (1H, t, J-7.5 Hz), 7.28 (2H, d, J-8.4 Hz), 7.51 (2H, d, J-8.4 Hz), 7.58 (1H, d, J-8.1 Hz), 8.28 (1H, dd, J-8.1 Hz), 9.20 (1H, d, J-1.8 Hz).

6-[4-(3-methyl-thio-2-butenoxy)phenyl]ethynyl nicotinic acid (Compound 12)

Using the same general procedure as for Compound 2 but using instead ethyl 6-[4-(3-methyl-thio-2-butenoxy)phenyl] ethynyl nicotinate (Compound 11), the title compound was prepared as a pale yellow solid. PMR (CDCl$_3$): & 1.67 (3H, s), 1.75 (3H, s), 3.61 (2H, d, J-7.5 Hz), 5.32 (1H, t, J-7.5 Hz), 7.30 (2H, d, J-8.4 Hz), 7.53 (2H, d, J-8.4 Hz), 7.61 (1H, d, J-8.7 Hz), 8.32 (1H, dd, J-8.7 Hz, 2.1 Hz), 9.23 (1H, d, J-2.1 Hz).

Using the method described for the preparation of ethyl 6-(4-tert butylphenyl)-ethynyl nicotinate (Compound 3), but using other examples of reagents corresponding to General Formula 2 and General Formula 3, respectively, numerous specific examples of compounds of the invention can be prepared. Still further, as examples, the ethyne compounds (General Formula 2) which were specifically described above, i.e.

4-tert-butylphenyl ethyne (Compound 19);
3-tert-butylphenyl ethyne (Compound 22);
4-(4-methylpentyl)-phenylethyne (Compound 26);
4-(1,1,4-trimethylpentyl)phenylethyne (Compound 32);
4-thio-tert-butoxyphenyl ethyne (Compound 39);
3-thio-tert-butoxyphenyl ethyne (Compound 43)
4-(3-methyl-thio-2-butenoxy)phenyl ethyne (Compound 44);
4-(3-methyl-thiobutoxy)-phenyl ethyne (Compound 48)
can be coupled with the reagents (General Formula 3) noted above, i.e. with
ethyl 2-(3-chloropyrid-5-yl)acetate;
ethyl 5-(2-chloropyrid-5-yl)pentanoate;
ethyl 2-(2-iodofur-5-yl)acetate;
ethyl 5-(2-iodofur-5-yl)pentanoate;
ethyl 2-(2-iodothien-5-yl)acetate;
ethyl 5-(2-iodothien-5-yl)pentanoate;
ethyl 2-(3-chloropyridazin-6-yl)acetate;
ethyl 5-(3-chloropyridazin-6-yl)pentanoate
to provide a large number of further examples of compounds of the invention.

Examples of Formulation for Topical Administration

Preferably the compounds of the invention may be administered topically using various formulation. Such formulations may be as follows:

| Ingredient | Weight/Percent |
| --- | --- |
| Solution | |
| Retinoid (active ingredient) | 0.1 |
| BHT | 0.1 |
| Alcohol USP | 58.0 |
| Polyesthylene Glycol 400 NF | 41.8 |

-continued

| Ingredient | Weight/Percent |
| --- | --- |
| Gel | |
| Retinoid (active ingredient) | 0.1 |
| BHT | 0.1 |
| Alcohol USP | 97.8 |
| Hydroxypropyl Cellulose | 2.0 |

What is claimed is:

1. A compound of the formula

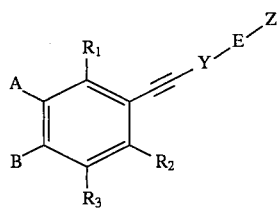

wherein $R_1$–$R_3$ independently are hydrogen, lower alkyl, lower cycloalkyl or lower alkenyl, A and B independently are hydrogen, lower alkyl, lower cycloalkyl, lower alkenyl, $SR_4$ or $OR_4$ where $R_4$ is lower alkyl, lower cycloalkyl or lower alkenyl;

Y is pyrimidinyl;

E is divalent lower alkenyl, lower alkynyl, lower cycloalkyl, lower branched chain alkyl, or is characterized by the formula $(CH_2)_n$ where n is 0–5, and Z is OH, $OCOR_5$, —COOH or a pharmaceutically acceptable salt, ester or amide thereof, or —CHO, $CH(OR_7)_2$, $CHOR_8O$, or $COR_9$ or $CR_9(OR_7)_2$, $CR_9OR_8O$, where $R_5$ is lower alkyl, phenyl or lower alkylphenyl, $R_7$ is lower alkyl, $R_8$ is a divalent alkyl radical of 2–5 carbons, and $R_9$ is an alkyl, cycloalkyl or alkenyl group having no more than 5 carbons.

2. A compounds or claim 1 wherein A and B independently are hydrogen, lower alkyl, cycloalkyl, or lower alkenyl.

3. A compounds of claim 2 wherein one of the A and B groups is lower alkyl.

4. A compounds of claim 3 wherein $R_1$–$R_3$ all are hydrogen.

5. A compounds of claim 2 wherein E is characterized by the formula $(CH_2)_n$, where n is 0–5.

6. A compounds of claim 2 wherein Z is —COOH or a pharmaceutically acceptable salt, ester or amide thereof.

7. A compounds of claim 6 wherein Z is a carboxylic acid ester.

8. A compound of claim 1 wherein one of the A and B groups is $SR_4$ where $R_4$ is lower alkyl, lower cycloalkyl or lower alkenyl.

9. A compounds of claim 8 wherein $R_1$–$R_3$ all are hydrogen.

10. A compounds of claim 8 wherein E is characterized by the formula $(CH_2)_n$ where n is 0–5.

11. A compounds of claim 8 wherein Z is —COOH or a pharmaceutically acceptable salt, ester or amide thereof.

12. A compounds of claim 11 wherein Z is carboxylic acid ester.

13. A pharmaceutically composition comprising an effective amount of a compound set forth in claim 1, for the treatment of acne, Darier's disease, psoriasis, icthyosis, eczema, atopic dermatitis, epithelial cancers, arthritic diseases, immunological disorders, dry eye syndrome, sun damage, disorders of gut epithelial differentiation, Krohn's disease, for preventing sun damage to skin and for promoting wound healing in combination with a pharmaceutically acceptable excipient.

* * * * *

UNITED STATES PATENT AND TRADEMARK OFFICE
CERTIFICATE OF CORRECTION

PATENT NO. : 5,516,904
DATED : May 14, 1996
INVENTOR(S) : Chandraratna

It is certified that error appears in the above-indentified patent and that said Letters Patent is hereby corrected as shown below:

Column 4, line 12, "$R_{10}$=H;" should be --$R_{10}$=H);--;
Column 4, line 21, "$R_{10}$=H;" should be --$R_{10}$=H);--;
Column 4, line 25, after "$R_{10}$=$CH_2$ $CH_3$" please add --)--;
Column 4, line 28, "$R_{10}$=H;" should be --$R_{10}$=H);--;
Column 4, line 42, "$R_{10}$=H;" should be --$R_{10}$=H).--;
Column 25, line 13, after"39" please delete")".
Column 4, in the structual formula "$CO_2R_{10}$*" should be --$CO_2R_{10}$--;
Column 5, line 29, "Containing" should be --containing--;
Column 7, line 31, "pd($PQ_3)_2Cl_2$" should be --Ps($PQ_3)_2Cl_2$--;
Column 14, in <u>Reaction Scheme 7</u>, compounds 36, 37 and 38, all occurrences of "R*" should be --$R_4$--;
Column 19, line 62, "Was" should be --was--;
Column 28, line 3, "or" should be --of--.

Signed and Sealed this

Eleventh Day of March, 1997

BRUCE LEHMAN

*Attest:*

*Attesting Officer*

Commissioner of Patents and Trademarks